(12) United States Patent
Geroni et al.

(10) Patent No.: US 7,642,229 B2
(45) Date of Patent: *Jan. 5, 2010

(54) PHARMACEUTICAL COMPOSITION AND A PRODUCT WHICH INCLUDES A SUBSTITUTED ACRYLOYL DISTAMYCIN DERIVATIVE, AN ANTIMICROTUBULE AGENT AND/OR AN ANTIMETABOLITE

(75) Inventors: Maria Cristina Rosa Geroni, Milan (IT); Paolo Cozzi, Milan (IT); Italo Beria, Nerviano (IT)

(73) Assignee: Nerviano Medical Sciences S.r.l., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/297,620

(22) PCT Filed: Jun. 20, 2001

(86) PCT No.: PCT/EP01/07060

§ 371 (c)(1), (2), (4) Date: Dec. 16, 2002

(87) PCT Pub. No.: WO01/97618

PCT Pub. Date: Dec. 27, 2001

(65) Prior Publication Data

US 2004/0092453 A1  May 13, 2004

(30) Foreign Application Priority Data

Jun. 23, 2000 (GB) .................................. 0015446.8

(51) Int. Cl.
*A61K 38/00* (2006.01)
*C07K 2/00* (2006.01)
(52) U.S. Cl. .......................................... 514/2; 530/300
(58) Field of Classification Search .................. 514/18, 514/449, 50, 251
See application file for complete search history.

(56) References Cited

U.S. PATENT DOCUMENTS

| | | | | |
|---|---|---|---|---|
| 5,597,830 | A * | 1/1997 | Klohs et al. | 514/283 |
| 5,633,274 | A * | 5/1997 | Halperin et al. | 514/405 |
| 5,646,177 | A | 7/1997 | Koch et al. | |
| 5,880,097 | A | 3/1999 | Lyttle et al. | |
| 6,066,654 | A * | 5/2000 | Gray et al. | 514/327 |
| 6,482,920 | B1 * | 11/2002 | Cozzi et al. | 530/331 |
| 6,576,612 | B1 * | 6/2003 | Fowst et al. | 514/18 |
| 7,030,089 | B2 * | 4/2006 | Geroni et al. | 514/17 |
| 2003/0161829 | A1 * | 8/2003 | Mascarenhas | 424/145.1 |
| 2004/0006023 | A1 * | 1/2004 | Fowst | 514/18 |
| 2005/0143315 | A1 * | 6/2005 | Geroni et al. | 514/18 |

FOREIGN PATENT DOCUMENTS

| | | |
|---|---|---|
| EP | 0 246 868 | 11/1987 |
| EP | 0 265 719 | 5/1988 |
| EP | 0 388 948 | 9/1990 |
| EP | 0 420 121 A1 | 4/1991 |
| GB | 2 178 036 | 2/1987 |
| WO | WO 90 11277 A | 10/1990 |
| WO | WO 96 05196 A | 2/1996 |
| WO | WO 97 28123 | 8/1997 |
| WO | WO 97 43258 | 11/1997 |
| WO | WO 98/04524 | 2/1998 |
| WO | WO 98/21202 | 5/1998 |
| WO | WO 99/34796 | 7/1999 |
| WO | WO 99 50265 A | 10/1999 |
| WO | WO 99/50266 | 10/1999 |
| WO | WO 00 06541 | 2/2000 |
| WO | WO 00 06542 | 2/2000 |
| WO | WO 01 40181 A | 6/2001 |
| WO | WO 01 85144 | 11/2001 |

OTHER PUBLICATIONS

C.J. Li, et al. Proc. Natl. Acad. Sci. USA (1999) 96(23), pp. 13369-13374.*
Stewart D J et al: "Non-Chemotherapeutic Agents That Potentiate Chemotherapy Efficacy" Cancer Treatment Reviews, vol. 16, No. 1, 1989, pp. 1-40, XP001039737 ISSN: 0305-7372 p. 18, paragraph 3 -p. 19, paragraph 1.
Baraldi, Pier Giovanni et al: "Synthesis and antitumor activity of novel distamycin derivatives" Bioorg. Med. Chem. Lett. (1996), 6(11), 1241-1246 XP004134862 p. 1241, paragraph 2 example Scheme1 p. 1244, paragraph 1 table 1 p. 1244, paragraph 4 -p. 1245, paragraph 1.
D'Alessio, Roberto et al: "Structure-activity relationship of novel distamycin A derivatives: Synthesis and antitumor activity" Bioorg. Med. Chem. Lett. (1994), 4(12), 1467-72, XP000671766.
Geroni Cristina et al: "Antitumor activity of PNU-166196, a novel DNA minor groove binder selected for clinical development." Proceedings of the American Association for Cancer Research Annual, No. 41, Mar. 2000, pp. 425-426, XP001039861 91st Annual Meeting of the American Association for Cancer Research.; San 2000, Mar. 2000, ISSN: 0197-016X.

(Continued)

*Primary Examiner*—Andrew D Kosar
(74) *Attorney, Agent, or Firm*—Scully, Scott, Murphy & Presser, P.C.

(57) ABSTRACT

A pharmaceutical composition and a product which includes an acryloyl distamycin derivative, an antimicrotubule agent and/or an antimetabolite useful in the treatment of tumors.

9 Claims, No Drawings

OTHER PUBLICATIONS

Colella, G. et al: "Mismatch repair deficiency is associated with resistance to DNA minor groove alkylating agents" Br. J. Cancer (1999), 80(3/4), 338-343, XP001039733.

Giusti Anna Maria et al: "In vivo induction of apoptosis with PNU-166196 in human ovarian carcinoma xenografts." Proceedings of the American Association for Cancer Research Annual, No. 41, Mar. 2000, p. 825 XP001039865 91st Annual Meeting of the American Association for Cancer Research.: San Francisco, California, USA; Apr. 1-5, 2000, Mar. 2000 ISSN: 0197-016X.

Tsuchida S et al: "Elevation of the Placental Glutathione-S-Transferase Form GST-PI in Tumor Tissues and the Levels in Sera of Patients With Cancer" Cancer Research, vol. 49, No. 18, 1989, pp. 5225-5229, XP001039783 ISSN: 0008-5472 abstract p. 5225, col. 1, paragraph 1 p. 5228, col. 1, paragraph 1 p. 5228, col. 2, paragraph 2.

Cozzi P: "A new class of cytotoxic DNA minor groove binders: alpha-halogenoacrylic derivatives of pyrrolecarbamoyl oligomers." Farmaco, (Jan.-Feb. 2001) 56 (1-2) 57-65., XP001039805 abstract p. 58, col. 2, paragraph 4 p. 59, col. 1, paragraph 1 figure 5 p. 60, col. 1, paragraph 2 -p. 61, col. 1, paragraph 4 tables 2,3 p. 62, col. 2, paragraph 3 figures 9, 10 table 5 p. 63, col. 1, paragraph 1 -col. 2, paragraph 2.

Baraldi, Pier Giovanni et al: "Synthesis and Antitumor Activity of New Benzoheterocyclic Derivatives of Distamycin A" J. Med. Chem. (2000), 43(14), 2675-2684 , Jul. 13, 2000, XP001039581 abstract p. 2676, col. 1; tables p. 2676, col. 1, paragraph 1 tables 1,2 p. 2678, col. 2, paragraph 5 -p. 2679, col. 1, paragraph 1 p. 2680, col. 2, paragraph 3.

Geroni C et al: "PNU-166196: A novel antitumor agent whose cytotoxicity is enhanced in tumor cells with high levels of glutathione." Tumori, vol. 86, No. 4 Suppl. 1, Jul. 2000, pp. 41-42, XP001039871 XV Congress of the Italian Cancer Society; Turin, Italy; Oct. 5-7, 2000 ISSN: 0300-8916.

Boger et al "Total Synthesis of Distamycin A and 2640 Analogues: A Solution-Phase combinatorial Approach to the Discovery of new Bioactive DNA Binding Agents and Development of a Rapid, High-Throughput Screen for Determining relative DNA Binding Affinity or DNA Binding Sequence Selectivity", J. Am. Chem. Soc. 2000, 122, 6382-6394.

Sola F et al: XP-002104215 "The antitumor efficacy of cytotoxic drugs is potentiated by treatment with PNU 145156E, a growth-complexing molecule" Cancer Chemotherapy and Pharmacology, Springer Verlag, Berlin, DE, vol. 43, No. 3, 1999, pp. 241-246, ISSN: 0344-5704.

Zou J P et al: XP-002104217 "Distamycin-A Derivatives Potentiate Tumor-Necrosis-Factor Activity Via The Modulation of Tyrosine Phosphorylation" International Journal of Cancer, New York, NY, US, vol. 72, No. 5, 1997, pp. 810-814, ISSN: 0020-7136.

Tagliabue G et al: XP004282511 "Combination of the New Minor Groove Alkylator Tallimustine and Melphalan" European Journal of Cancer, Pergamon Press, Oxford, GB, vol. 33, No. 2, Feb. 1997, pp. 284-287, ISSN: 0959-8049.

Cozzi P et al: XP004200573 "Cytotoxic alpha-Bromoacrylic Derivatives of Distamycin Analogues Modified at the Amidino Moiety" Bioorganic & Medicinal Chemistry Letters, Oxford, GB, vol. 10, No. 11, Jun. 2000, pp. 1273-1276, ISSN: 0960-894X.

Cozzi P et al: XP004200572 "Cytotoxic Halogenoacrylic Derivatives of Distamycin A" Bioorganic & Medicinal Chemistry Letters, Oxford, GB, vol. 10, No. 11, Jun. 2000, pp. 1269-1272, ISSN: 0960-894X.

Catharina J A Van Moorsel et al: XP002110339 "Gemcitabine: Futrue Prospects of Single-Agent and Combination Studies" Oncologist, Alphamed Press, US, vol. 2, No. 3, 1997, pp. 127-134, ISSN: 1083-7159.

Mosconi A M et al: XP004282426 "Combination Therapy with Gemcitabine in Non-small Cell Lung Cancer" European Journal of Cancer, Pergamon Press, Oxford, GB, vol. 33, Jan. 1997, pp. S14-S17, ISSN: 0959-8049.

Budavari S (ED): XP002191966 "The Merck Index (12th Edition)" Merck Index, Encyclopedia of Chemicals, Drugs, and Biologicals, 13th. Edition 1996, Whitehouse Station, Merck & Co, US, vol. ed. 13, 2001, p. 4206 ISBN: 0-911910-12-3.

* cited by examiner

PHARMACEUTICAL COMPOSITION AND A PRODUCT WHICH INCLUDES A SUBSTITUTED ACRYLOYL DISTAMYCIN DERIVATIVE, AN ANTIMICROTUBULE AGENT AND/OR AN ANTIMETABOLITE

REFERENCE TO RELATED APPLICATIONS

The present application is a national phase application, filed under 35 U.S.C. §371, based on PCT Application Serial No. PCT EP01/07060, filed Jun. 20, 2001.

The present invention relates to the field of cancer treatment and provides an antitumor composition comprising a substituted acryloyl distamycin derivative, more particularly an α-bromo- or α-chloro-acryloyl distamycin derivative, an antimicrotubule agent and/or an antimetabolite, having a synergistic antineoplastic effect.

Distamycin A and analogues thereof, hereinafter referred to as distamycin and distamycin-like derivatives, are known in the art as cytotoxic agents useful in antitumor therapy.

Distamycin A is an antibiotic substance with antiviral and antiprotozoal activity, having a polypyrrole framework [*Nature* 203: 1064 (1964); *J. Med. Chem.* 32: 774-778 (1989)]. The international patent applications WO 90/11277, WO 98/04524, WO 98/21202, WO 99/50265, WO 99/50266 and WO 01/40181 (claiming priority from British patent application No. 9928703.9), all in the name of the applicant itself and herewith incorporated by reference, disclose acryloyl distamycin derivatives wherein the amidino moiety of distamycin is optionally replaced by nitrogen-containing ending groups such as, for instance, cyanamidino, N-methylamidino, guanidino, carbamoyl, amidoxime, cyano and the like, and/or wherein the polypyrrole framework of distamycin, or part of it, is replaced by varying carbocyclic or heterocyclic moieties.

The present invention provides, in a first aspect, a pharmaceutical composition for use in antineoplastic therapy in mammals, including humans, comprising a pharmaceutically acceptable carrier or excipient;

an acryloyl distamycin derivative of formula (I):

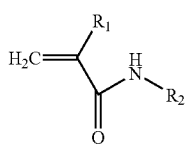

wherein:
$R_1$ is a bromine or chlorine atom;
$R_2$ is a distamycin or distamycin-like framework; or a pharmaceutically acceptable salt thereof; and
an antimicrotubule agent and/or an antimetabolite.

The present invention includes, within its scope, the pharmaceutical compositions comprising any of the possible isomers covered by the compounds of formula (I), both considered separately or in admixture, as well as the metabolites and the pharmaceutically acceptable bio-precursors (otherwise known as pro-drugs) of the compounds of formula (I).

In the present description, unless otherwise specified, with the term distamycin or distamycin-like framework $R_2$ we intend any moiety structurally closely related to distamycin itself, for instance by optionally replacing the ending amidino moiety of distamycin and/or its polypyrrole framework, or part of it.

Antimicrotubule agents and antimetabolites are widely known in the art as antitumor agents; see, for a general reference, Cancer, Principles and Practice of Oncology, Lippincott-Raven Ed. (1997), 432-452 and 467-483

According to a preferred embodiment of the invention, herewith provided are the above pharmaceutical compositions wherein the antimicrotubule agents are, for instance, taxanes, e.g. paclitaxel or docetaxel; vinca alkaloids, e.g. vincristine, vinblastine, vindesine, vinorelbine; and estramustine, optionally encapsulated within liposomes.

Preferred antimetabolites are, for instance, antifolates, e.g. metotrexate, trimetrexate, tomudex; 5-fluoropyrimidines, e.g. 5-FU, floxuridine, ftorafur and capecitabine; cytidine analogs, e.g. cytarabine, azacitidine and gemcitabine.

Particularly preferred antimicrotubule agents are paclitaxel and estramustine whereas preferred antimetabolites are 5-fluorouracil or gemcitabine.

According to another preferred embodiment of the invention, herewith provided are the above pharmaceutical compositions wherein, within the acryloyl distamycin derivative of formula (I), $R_1$ has the above reported meanings and $R_2$ is a group of formula (II) below:

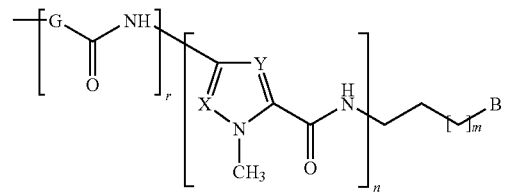

wherein
m is an integer from 0 to 2;
n is an integer from 2 to 5;
r is 0 or 1;
X and Y are, the same or different and independently for each heterocyclic ring, a nitrogen atom or a CH group;
G is phenylene, a 5 or 6 membered saturated or unsaturated heterocyclic ring with from 1 to 3 heteroatoms selected among N, O or S, or it is a group of formula (III) below:

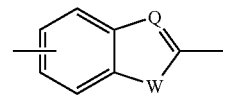

wherein Q is a nitrogen atom or a CH group and W is an oxygen or sulfur atom or it is a group $NR_3$ wherein $R_3$ is hydrogen or $C_1$-$C_4$ alkyl;
B is selected from the group consisting of

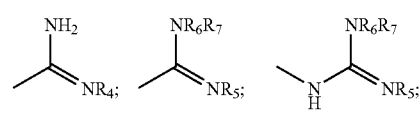

-continued

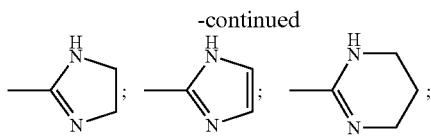

—CN; —NR$_5$R$_6$; —CONR$_5$R$_6$; —NHCONR$_5$R$_6$ wherein R$_4$ is cyano, amino, hydroxy or C$_1$-C$_4$ alkoxy; R$_5$, R$_6$ and R$_7$, the same or different, are hydrogen or C$_1$-C$_4$ alkyl.

In the present description, unless otherwise specified, with the term C$_1$-C$_4$ alkyl or alkoxy group we intend a straight or branched group selected from methyl ethyl, n-propyl isopropyl, n-butyl, isobutyl, sec-butyl, tert-butyl, methoxy, ethoxy, n-propoxy, isopropoxy, n-butoxy, isobutoxy, see-butoxy or tert-butoxy.

Even more preferred are the pharmaceutical compositions of the invention comprising the above acryloyl distamycin derivative of formula (I) wherein R$_1$ is bromine or chlorine; R$_2$ is the above group of formula (II) wherein r is 0, m is 0 or 1, n is 4 and B has the above reported meanings.

Still more preferred, within this class, are the pharmaceutical compositions comprising the compounds of formula (I) wherein R$_1$ is bromine or chlorine; R$_2$ is the above group of formula (II) wherein r is 0, m is or 1, n is 4, X and Y are both CH groups and B is selected from:

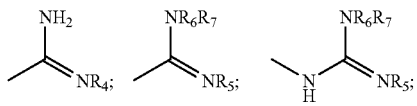

—CN; —CONR$_5$R$_6$; —NHCONR$_5$R$_6$ wherein R$_4$ is cyano or hydroxy and R$_5$, R$_6$ and R$_7$, the same or different, are hydrogen or C$_1$-C$_4$ alkyl.

Pharmaceutically acceptable salts of the compounds of formula (I) are those with pharmaceutically acceptable inorganic or organic acids such as, for instance, hydrochloric, hydrobromic, sulfuric, nitric, acetic, propionic, succinic, malonic, citric, tararic, methanesulfonic, p-toluenesulfonic acid and the like.

Examples of preferred acryloyl distamycin derivatives of formula (I), within the compositions object of the invention, optionally in the form of pharmaceutically acceptable salts, preferably with hydrochloric acid, are:
1. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
2. N-(5-{[(5-{[(5-{[(2-{[amino(imino)methyl]amino}propyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
3. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
4. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-imidazole-2-carboxamide hydrochloride;
5. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide hydrochloride;
6. N-(5-{[(5-{[(5-{[(3-amino-3-oxopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;
7. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-chloroacryloyl)amino]-1-methyl-1H-pyrrole-2-carboxamide hydrochloride;
8. N-(5-{[(5-{[(3-{[amino(imino)methyl]amino}propyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
9. N-(5-{[(5-{[(3-amino-3-iminopropyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride; and
10. N-{5-[({5-[({5-[({3-[(aminocarbonyl)amino]propyl}amino)carbonyl]-1-methyl-1H-pyrrol-3-yl}amino)carbonyl]-1-methyl-1H-pyrrol-3-yl}amino)carbonyl]-1-methyl-1H-pyrrol-3-yl}-4-[(2-bromoacryloyl)amino]-1-methyl-1H-pyyrole-2-carboxamide.

The above compounds of formula (I), either specifically identified as such or by means of the general formula, are known or easily prepared according to known methods as reported, for instance, in the aforementioned international patent applications WO 90/11277, WO 98/04524, WO 98/21202, WO 99/50265 and WO 99/50266 and WO 01/40181.

The present invention further provides a product comprising an acryloyl distamycin derivative of formula (I), as defined above, an antimicrotubule agent and/or an antimetabolite, as a combined preparation for simultaneous, separate or sequential use in antitumor therapy.

Particularly preferred, in this respect, is a product comprising N-(5-{[(5-{[(5-{[(2-[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride (internal code PNU 166196) and gemcitabine, as a combined preparation for simultaneous, separate or sequential use in antitumor therapy.

A further aspect of the present invention is to provide a method of treating a mammal, including humans, suffering from a neoplastic disease state, which method comprises administering to said mammal the above acryloyl distamycin derivative of formula (I), an antimicrotubule agent and/or an antimetabolite, in amounts effective to produce a synergistic antineoplastic effect.

The present invention also provides a method for lowering the side effects caused by antineoplastic therapy with an antineoplastic agent in a mammal in need thereof, including human, the method comprising administering to said mammal a combined preparation comprising an acryloyl distamycin derivative of formula (I), an antimicrotubule agent and/or an antimetabolite, in amounts effective to produce a synergistic antineoplastic effect.

By the term "synergistic antineoplastic effect", as used herein, it is meant the inhibition of the growth tumor, preferably the complete regression of the tumor, by administering an effective amount of the combination comprising an acryloyl distamycin derivative of formula (I), an antimicrotubule agent and/or an antimetabolite to mammals, including humans.

By the term "administered" or "administering", as used herein, it is meant parenteral and/or oral administration; the term "parenteral" means intravenous, subcutaneous and intramuscular administration.

In the method of the present invention, the acryloyl distamycin derivative may be administered simultaneously with the antimicrotubule agent or with the antimetabolite. Alternatively, the two drugs maybe administered sequentially in either order.

When the acryloyl distamycin derivative is administered with both the antimicrotubule agent and the antimetabolite, according to an embodiment of the invention, the drugs are preferably administered sequentially, in any order.

In this respect, it will be appreciated that the actual preferred method and order of administration will vary according to, inter alias, the particular formulation of the acryloyl distamycin of formula (I) being used, the particular formulation of the antimicrotubule agent and/or the antimetabolite being used, the particular tumor model being treated as well as the particular host being treated.

To administer the acryloyl distamycin derivative of formula (I), according to the method of the invention, the course of therapy generally employed comprises doses varying from about 0.05 to about 100 mg/m² of body surface area and, more preferably, from about 0.1 to about 50 mg/m² of body surface area.

For the administration of the taxanes, according to the method of the invention, the course of therapy generally employed comprises doses varying from about 1 to about 1000 mg/m² of body surface area and, more preferably, from about 10 to about 500 mg/m² of body surface area.

For the administration of the vinca alkaloids, according to the method of the invention, the course of therapy generally employed comprises doses varying from about 0.1 to about 1000 mg/m² of body surface area and, more preferably, from about 0.5 to about 100 mg/m² of body surface area.

For the administration of the antimetabolite according to the invention, the course of therapy generally employed comprises doses varying from about 0.1 to about 10 g/m² of body surface area and, more preferably, from about 1 to about 5 g/m² of body surface area.

The antineoplastic therapy of the present invention is particularly suitable for treating breast, ovary, lung, colon, kidney, stomach, pancreas, liver, melanoma, leukemia and brain tumors in mammals, including humans.

In a further aspect, the present invention is directed to a composition comprising an effective amount of an acryloyl distamycin derivative of formula (I), as defined above, an antimicrotubule agent and/or an antimetabolite, in the preparation of a medicament for use in the prevention or treatment of metastasis or in the treatment of tumors by inhibition of angiogenesis.

As stated above, the effect of an acryloyl distamycin derivative of formula (I) with an antimicrotubule agent and/or an antimetabolite, is significantly increased without a parallel increase of toxicity. In other words, the combined therapy of the present invention enhances the antitumoral effects of the acryloyl distamycin derivative and of the other drug, being either an antimicrotubule, an antimetabolite or a combination thereof and, hence, provides the most effective and least toxic treatment for tumors.

The superadditive effects of the combined preparations of the invention are shown, for instance, by the following in vivo antitumor activity data which are intended to illustrate the present invention without posing any limitation to it.

Table 1 shows the antileukemic activity on disseminated L1210 murine leukemia obtained by combining N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride, as a representative compound of formula (I)—internal code PNU 166196, with gemcitabine.

At the dose of 15 mg/kg of gemcitabine alone (day +1 after tumor injection, 2 h after PNU 166196 administration) and at the dose of 0.7 mg/kg of PNU 166196 alone (days +1,6) were associated, without toxicity, ILS % values of 50 and 58, respectively. Combining gemcitabine and PNU 166196 at the same doses with the same schedule, an increase of activity with ILS % values of 127 were observed, thus indicating a synergistic effect.

TABLE 1

Antileukemic activity against disseminated L1210[1] murine leukemia of an acryloyl distamycin derivative (I) in combination with gemcitabine.

| Compound | Treatment schedule | Dose[2] (mg/kg/day) | ILS %[3] | Tox[4] |
|---|---|---|---|---|
| PNU 166196 | iv + 1.6 | 0.78 | 58 | 0/10 |
| Gemcitabine | iv + 1 (*) | 15 | 50 | 0/10 |
| PNU 166196 + | iv + 1.6 | 0.78+ | 127 | 0/10 |
| Gemcitabine | iv + 1 | 15 | | |

[1]L1210 leukemia cells (10⁵/mouse) are injected iv on day 0.
[2]Treatment is given starting on day 1 after tumor transplantation (day 0).
[3]Increase in life span: [(median survival time of treated mice/median survival time of controls) × 100] − 100
[4]Number of toxic deaths/number of mice.
(*) treatment 2 h after PNU 166196 administration.

The invention claimed is:

1. A pharmaceutical composition comprising a pharmaceutically acceptable carrier or excipient and, as active ingredient, an acryloyl distamycin derivative of formula (I):

wherein:
$R_1$ is a bromine or chlorine atom;
$R_2$ is a group of formula (II)

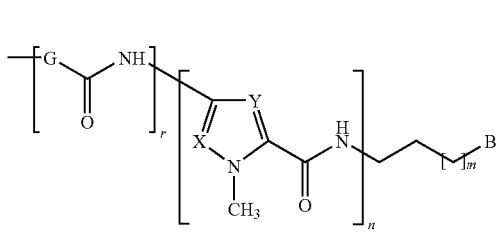

wherein
m is an integer from 0 to 2;
n is an integer from 2 to 5;
r is 0 or 1;
X and Y are the same or different and are independently, for each heterocyclic ring, a nitrogen atom or a CH group;
G is phenylene, a 5 or 6 membered saturated or unsaturated heterocyclic ring with from 1 to 3 heteroatoms selected from the group consisting of N, O and S, or a group of formula III

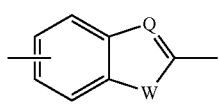

whererin Q is a nitrogen atom or a CH group; and W is an oxygen or sulfur atom or an $NR_3$ group, wherein $R_3$ is a hydrogen or $C_1$-$C_4$ alkyl;
B is selected from the group consisting of

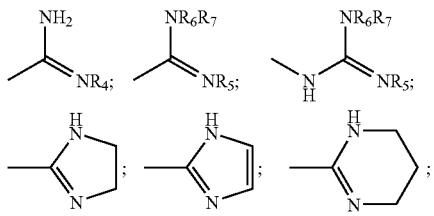

—CN; —$NR_5R_6$; —$CONR_5R_6$; —$NHCONR_5R_6$
wherein $R_4$ is cyano, amino, hydroxyl or $C_1$-$C_4$ alkoxy; $R_5$, $R_6$ and $R_7$ are the same or different and are hydrogen or $C_1$-$C_4$ alkyl; or a pharmaceutically acceptable salt thereof and an antimicrotubule agent, wherein the antimicrotubule agent is docetaxel.

2. The pharmaceutical composition according to claim 1 wherein r is 0, m is 0 or 1, and n is 4.

3. The pharmaceutical composition according to claim 2 wherein X and Y are both CH groups and B is selected from the group consisting of:

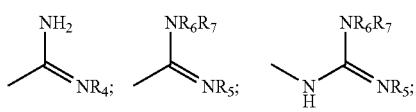

—CH; —$CONR_5R_6$; and —$NHCONR_5R_6$,
wherein $R_1$ is cyano or hydroxy and $R_5$, $R_5$ and $R_7$ are the same or different and are hydrogen or $C_1$-$C_4$ alkyl.

4. The pharmaceutical composition according to claim 1 wherein said acryloyl distamycin derivative, optionally in the form of a pharmaceutically acceptable salt, is selected from the group consisting of:

(1) N(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbon- yl}-1-methyl-1H-pyrrol-3-yl)-4-[(2-bromoacryloyl)amino]-1methyl-1H-pyrrole-2-carboxamide hydrochloride;

(2) N(5-{[(5-{[(5-{[(2-{[amino(imino)methyl]amino}propyl)amino]carbonyl}-1-methyl-1H-pyrrol-3yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

(3) N-5-{[(5-{[(5-{[(3-amino-3-iminopropyl)amino]carbonyl}-1-methyl-1H-pyrrol-3-yl)amino]carbonyl}-1-methyl-1H-pyrrol-3yl)amino]carbonyl}-1-methyl-1H-pyrrol-3-yl)-4-[(2-bromoacryloyl)amino]-1-methyl-1H-pyrrole-2-carboxamide hydrochloride;

(4) N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-imidazole-2-carboxamide hydrochloride;

(5) N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide hydrochloride;

(6) N-(5-{[(5-{[(5-{[(3-amino-3-oxopropyl)amino]carbonyl}- 1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;

(7) N-(5-{[(5-{[(5-{[(2-{[amino(imino)methyl]amino}ethyl)amino]carbonyl}-1-methyl-1H-pyrrol-3-yl)amino]carbonyl}-1methyl-1H-pyrrol-3-yl)amino]carbonyl}-1-methyl-1H-pyrrol-3-yl)-4-[(2-chloroacryloyl)amino]-1-methyl-1H-pyrrole-2-carboxamide hydrochloride;

(8) N-(5-{[(5-{[(3-{[amino(imino)methyl]am1-amino}propyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

(9) N-5-{[(5-{[(3-amino-3-iminopropyl)amino]carbonyl}-1-methyl-1H-pyrrol-3-yl)amino]carbonyl}-1-methyl-1H-pyrrol-3-yl)-4-[(2-bromo-acryloyl)amino]-1-methyl-1H-pyrrole-2-carboxamide hydrochloride; and

(10) N-{5-[({5-[({5-[({3-[(aminocarbonyl)amino]propyl}amino)carbonyl]-1-methyl-1H-pyrrol-3-yl}amino)carbonyl]-1-methyl-1H-pyrrol-3-yl}amino)carbonyl]-1-methyl-1H-pyrrol-3-yl}-4-[(2-bromoacryloyl)amino]-1-methyl-1H-pyyrole-2-carboxamide.

5. The pharmaceutical composition according to claim 1 wherein said acryloyl distamycin derivative of formula (I) is PNU 166196.

6. A method of treating a mammal suffering from a neoplastic disease state, comprising administering to said mammal an acryloyl distamycin derivative of formula (I):

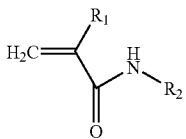

(I)

wherein:
R₁ is a bromine or chlorine atom;
R₂ is a group of formula (II)

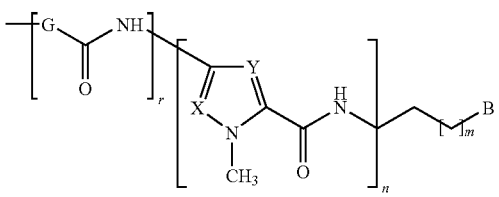

(II)

wherein
m is an integer from 0 to 2;
n is an integer from 2 to 5;
r is 0 or 1;
X and Y are the same or different and are independently, for each heterocyclic ring, a nitrogen atom or a CH group;
G is phenylene, a 5 or 6 membered saturated or unsaturated heterocyclic ring with from 1 to 3 heteroatoms selected from the group consisting of N, O and S, or a group of formula III

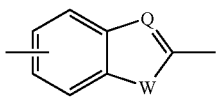

(III)

whererin Q is a nitrogen atom or a CH group; and W is an oxygen or sulfur atom or an NR₃ group, wherein R₃ is a hydrogen or C₁-C₄ alkyl;
B is selected from the group consisting of

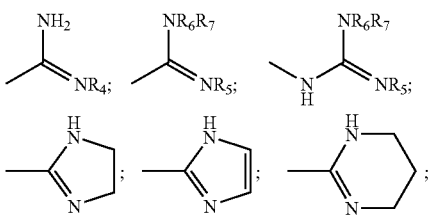

—CN; —NR₅R₆; —CONR₅R₆; —NHCONR₅R₆
wherein R₄ is cyano, amino, hydroxyl or C₁-C₄ alkoxy; R₅, R₆ and R₇ are the same or different and are hydrogen or C₁-C₄ alkyl; or a pharmaceutically acceptable salt thereof;
and an antimicrotubule agent, wherein the antimicrotubule agent is docetaxel, in amounts effective to produce a synergistic antineoplastic effect, wherein the neoplastic disease state is selected from the group consisting of breast, ovary, lung, colon, kidney, stomach, pancreas, liver, melanoma, leukemia and brain tumors.

7. The method according to claim 6 wherein the acryloyl distamycin derivative is selected from the group consisting of:

(1) N(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbon- yl}-1-methyl-1H-pyrrol-3-yl)-4-[(2-bromoacryloyl)amino]-1methyl-1H-pyrrole-2-carboxamide hydrochloride;

(2) N(5-{[(5-{[(5-{[(2-{[amino(imino)methyl]amino}propyl)amino]carbonyl}-1-methyl-1H-pyrrol-3yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

(3) N-5-{[(5-{[(5-{[(3-amino-3-iminopropyl)amino]carbonyl}-1-methyl-1H-pyrrol-3-yl)amino]carbonyl}-1-methyl-1H-pyrrol-3yl)amino]carbonyl}-1-methyl-1H-pyrrol-3-yl)-4-[(2-bromoacryloyl)amino]-1-methyl-1H-pyrrole-2-carboxamide hydrochloride;

(4) N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}- 1-methyl-1H-pyrrol-3-yl)-4-[(2-bromoacryloyl)amino]-1-methyl-1H-imidazole-2-carboxamide hydrochloride;

(5) N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide hydrochloride;

(6) N-(5 -{[(5-{[(5-{[(3-amino-3-oxopropyl)amino]carbonyl}- 1-methyl-1H-pyrrol-3-yl)amino]carbonyl}-1-methyl-1H-pyrrol-3-yl)amino]carbonyl}- 1-methyl-1H-pyrrol-3-yl)-3-[(2-bromoacryloyl)amino]-1-methyl-1H-pyrazole-5-carboxamide;

(7) N-(5-{[(5-{[(5-{[(2-{[amino(imino)methyl]amino}ethyl)amino]carbonyl}-1-methyl-1H-pyrrol-3-yl)amino]carbonyl}-1methyl-1H-pyrrol-3-yl)amino]carbonyl}- 1-methyl-1H-pyrrol-3-yl)-4-[(2-chloroacryloyl)amino]-1-methyl-1H-pyrrole-2-carboxamide hydrochloride;

(8) N-(5-{[(5-{[(3-{[amino(imino)methyl]amino}propyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

(9) N-5-{[(5-{[(3-amino-3-iminopropyl)amino]carbonyl}-1-methyl-1H-pyrrol-3-yl)amino]carbonyl}-1-methyl-1H-pyrrol-3-yl)-4-[(2-bromo-acryloyl)amino]-1-methyl-1H-pyrrole-2-carboxamide hydrochloride; and

(10) N-{5-[({5-[({5-[({3-[(aminocarbonyl)amino]propyl}amino)carbonyl]-1-methyl-1H-pyrrol-3-yl}amino)carbonyl]-1-methyl-1H-pyrrol-3-yl}amino)carbonyl]-1-methyl-1H-pyrrol-3-yl}-4-[(2-bromoacryloyl)amino]-1-methyl-1H-pyyrole-2-carboxamide.

8. A method for lowering the side effects caused by antineoplastic therapy with an antineoplastic agent, in a mammal in need thereof, comprising administering to said mammal a combined preparation comprising an acryloyl distamycin derivative of formula (I):

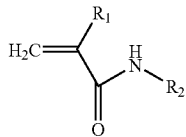

wherein:
R₁ is a bromine or chlorine atom;
R₂ is a group of formula (II)

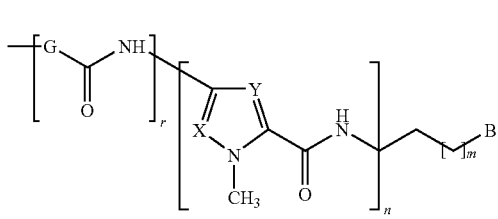

wherein
m is an integer from 0 to 2;
n is an integer from 2 to 5;
r is 0 or 1;
X and Y are the same or different and are independently, for each heterocyclic ring, a nitrogen atom or a CH group;
G is phenylene, a 5 or 6 membered saturated or unsaturated heterocyclic ring with from 1 to 3 heteroatoms selected from the group consisting of N, O and S, or a group of formula III

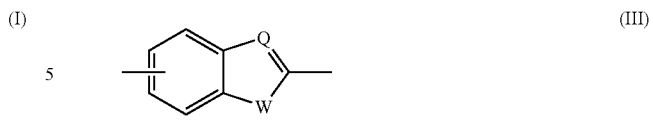

whererin Q is a nitrogen atom or a CH group; and W is an oxygen or sulfur atom or an $NR_3$ group, wherein $R_3$ is a hydrogen or $C_1$-$C_4$ alkyl;
B is selected from the group consisting of —CN; —$NR_5R_6$; —$CONR_5R_6$; —$NHCONR_5R_6$
wherein $R_4$ is cyano, amino, hydroxyl or $C_1$-$C_4$ alkoxy; $R_5$, $R_6$ and $R_7$ are the same or different and are hydrogen or $C_1$-$C_4$ alkyl; or a pharmaceutically acceptable salt thereof;
and an antimicrotubule agent, wherein the antimicrotubule agent is docetaxel, in amounts effective to produce a synergistic antineoplastic effect.

9. The method according to claim 6 or 8, wherein the mammal is a human.

* * * * *